(12) United States Patent
Matsui et al.

(10) Patent No.: US 9,739,759 B2
(45) Date of Patent: Aug. 22, 2017

(54) RESIN MEMBER WITH GAS PERMEABLE MEMBER AND METHOD OF MANUFACTURING THE SAME, CASING, AND SENSOR

(71) Applicant: NGK SPARK PLUG CO., LTD., Nagoya, Aichi (JP)

(72) Inventors: Ryosuke Matsui, Kiyosu (JP); Takashi Koda, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 0 days.

(21) Appl. No.: 14/826,764

(22) Filed: Aug. 14, 2015

(65) Prior Publication Data

US 2016/0109419 A1    Apr. 21, 2016

(30) Foreign Application Priority Data

Aug. 26, 2014  (JP) .................................. 2014-171138
Jul. 20, 2015  (JP) .................................. 2015-143545

(51) Int. Cl.
*G01N 33/00* (2006.01)
*B01D 46/00* (2006.01)
(Continued)

(52) U.S. Cl.
CPC ..... *G01N 33/0009* (2013.01); *B01D 46/0002* (2013.01); *B01D 46/10* (2013.01);
(Continued)

(58) Field of Classification Search
CPC  B01D 46/0002; B01D 46/10; B01D 46/0004; B01D 46/0005; B01D 46/0016;
(Continued)

(56) References Cited

U.S. PATENT DOCUMENTS 6,827,232 B1 *  12/2004  Hara ................. B29C 45/14336
                                                      220/371
2010/0221995 A1 *  9/2010  Furuyama ............... B29C 65/08
                                                      454/284

FOREIGN PATENT DOCUMENTS

DE        1 955 033       6/1970
GB        1 271 860       4/1972
JP        2005-231276 A   9/2005

OTHER PUBLICATIONS

Office Action dated Nov. 30, 2016 for corresponding German Application No. 10 2015 010 501.9.

* cited by examiner

*Primary Examiner* — Daniel S Larkin
(74) *Attorney, Agent, or Firm* — Sughrue Mion, PLLC

(57) ABSTRACT

A resin member with a gas permeable member (8) includes a resin member having at least one gas hole (20h) extending therethrough between a front surface (8a) and a back surface (8b), and a sheet-like gas permeable member (50) covering the gas hole. An outer circumferential portion (50p) of the gas permeable member is embedded in the resin member. The resin member further includes first recesses (22) disposed around the gas hole, depressed from at least one of the front surface and back surfaces, and allowing at least a portion of the gas permeable member to be visible in a front-back direction, and second recesses (24) disposed externally of an outer peripheral edge (50e) of the gas permeable member and depressed from at least one of the front surface and the back surface and through which the gas permeable member is invisible in the front-back direction.

5 Claims, 10 Drawing Sheets

(51) Int. Cl.
  *B01D 46/10* (2006.01)
  *B29C 45/14* (2006.01)
  *B29L 31/00* (2006.01)
(52) U.S. Cl.
  CPC ................... *B29C 45/14065* (2013.01); *B29C 2045/14122* (2013.01); *B29K 2995/0065* (2013.01); *B29L 2031/752* (2013.01)
(58) Field of Classification Search
  CPC .......... B29C 2045/14122; B29C 33/12; B29C 45/14; B29C 45/14065; B29K 2995/0065; B29L 2031/752; G01N 33/0009; G01N 1/2208; G01N 2001/2223; G01N 1/2273; G01N 1/26; G01N 2015/0261
  See application file for complete search history.

RESIN MEMBER WITH GAS PERMEABLE MEMBER AND METHOD OF MANUFACTURING THE SAME, CASING, AND SENSOR

TECHNICAL FIELD

The present invention relates to a resin member with a gas permeable member which allows gas to flow into and out from the interior thereof, a method of manufacturing the same, a casing, and a sensor.

BACKGROUND ART

In recent years, in consideration of demand of society, such as environmental protection and nature conservation, research has been actively conducted on a fuel cell, which is an efficient and clean energy source. In particular, a polymer electrolyte fuel cell (PEFC) and a hydrogen internal combustion engine, which operate at low temperature, have high output, and are high in density, are expected to be used in homes or be mounted on vehicles. However, since these energy sources use hydrogen as fuel, they require a sensor for detecting leakage of hydrogen.

Thus, a sensor for detecting the concentration of inflammable gas such as hydrogen has a structure in which a sensor element is housed in a resin case with a gas permeable member and measures the concentration of gas flowing in and out through a gas hole. A known case member serving as such a resin case has a structure in which an annular groove is formed around a gas hole (opening) by insert molding using a slide mold, and a circumferential portion of a gas permeable porous membrane is embedded in resin around the gas hole and in the vicinity of the annular groove, whereby the gas hole is covered with the gas permeable porous membrane (see Patent Document 1).

PRIOR ART DOCUMENT

Patent Document

[Patent Document 1] Japanese Patent Application Laid-Open (kokai) No. 2005-231276 (FIGS. 3 and 7)

SUMMARY OF THE INVENTION

Problem to be Solved by the Invention

Incidentally, since the gas permeable member to cover the gas hole has the form of a sheet, such as a metal mesh or a resin filter, in injection-molding the resin case, molding pressure of molten resin may deform the gas permeable member in a mold or may positionally shift the gas permeable member from the position of the gas hole in the mold. The deformation of the gas permeable member leads to a defective product, causing deterioration in yield. In the case where an outer circumferential portion of the gas permeable member partially fails to be embedded in resin as a result of a positional shift of the gas permeable member from the position of the gas hole, a gap is formed between the gas permeable member and the inner circumference of the gas hole, potentially resulting in insufficient performance of an explosion prevention function of preventing blowout, to the outside of the case, of flame of hydrogen gas which ignites inside the case. However, difficulty is encountered in checking to see whether or not a gap is formed between the gas permeable member and the inner circumference of the gas hole; therefore, the checking work consumes labor, resulting in deterioration in productivity.

Thus, an object of the present invention is to provide a resin member with a gas permeable member whose structure allows restraint of deformation of the gas permeable member, allows the gas permeable member to completely cover a gas hole, and allows easy checking to see whether or not the gas permeable member completely covers the gas hole, a method of manufacturing the same, a casing, and a sensor.

Means for Solving the Problem

In order to solve the above-described problem, the present invention provides a resin member with a gas permeable member comprising a resin member having at least one gas hole extending therethrough between a front surface and a back surface thereof, and a sheet-like gas permeable member being larger in outline than the gas hole and covering the gas hole in a gas permeable manner. An outer circumferential portion of the gas permeable member is embedded in the resin member. The resin member with a gas permeable member further comprises a first recess disposed around the gas hole, depressed from at least one of the front surface and the back surface, and allowing at least a portion of the gas permeable member to be visible in a front-back direction, and a second recess which is disposed externally of an outer peripheral edge of the gas permeable member and depressed from at least one of the front surface and the back surface and through which the gas permeable member is invisible in the front-back direction.

Since the first recess is disposed radially outward of the gas hole, when at least a portion of the gas permeable member is visible through the first recess, it indicates that the outer peripheral edge of the gas permeable member is located radially outward of the gas hole; i.e., the gas permeable member completely covers the gas hole. Therefore, according to this resin member with a gas permeable member, by means of observing the first recess in the front-back direction, whether or not the gas permeable member completely covers the gas hole can be easily checked. The second recess is a portion which is not filled with resin because of existence of a core (protrusion) in a mold in the course of resin-molding the resin member with a gas permeable member, and the protrusion surrounds the outer peripheral edge of the gas permeable member. Therefore, according to this resin member with a gas permeable member, the second recess prevents a planar positional shift of the gas permeable member, which could otherwise result from flow of molten resin in molding, whereby the occurrence of product defects can be reduced.

In the resin member with a gas permeable member of the present invention, the first recess may not extend between the front surface and the back surface.

According to this resin member with a gas permeable member, since the first recess does not extend between the front surface and the back surface, even when a portion of the gas permeable member and a region of nonexistence of the gas permeable member are visible through the first recess, gas does not flow through the region instead of flowing through the gas permeable member.

In the resin member with a gas permeable member of the present invention, the first recess may be formed in the front surface and in the back surface.

According to this resin member with a gas permeable member, since observation through the first recess is possible from the front surface and from the back surface, whether or not the gas permeable member completely covers the gas hole can be more easily checked.

In the resin member with a gas permeable member of the present invention, the first recess and the second recess may not overlap each other as viewed from the center of the gas hole in a direction orthogonal to a direction directed from the front surface to the back surface.

The first recess and the second recess cause reduction in associated wall thickness due to depression and thus cause reduction in strength. Thus, in the case where the first recess and the second recess overlap each other with respect to a circumferential position, an overlapping region may possibly greatly reduce in strength. Therefore, by means of the first recess and the second recess being arranged not to overlap each other with respect to a circumferential position, reduction in strength can be prevented.

The present invention provides a method of manufacturing a resin member with a gas permeable member by injecting molten resin, for molding, into a cavity formed between a first mold and a second mold. The resin member with a gas permeable member comprises a resin member having at least one gas hole extending therethrough between a front surface and a back surface thereof, and a sheet-like gas permeable member being larger in outline than the gas hole and covering the gas hole in a gas permeable manner. An outer circumferential portion of the gas permeable member is embedded in the resin member. The first mold and the second mold have respectively at least one center protrusion which comes into contact with a central portion of the gas permeable member excluding the outer circumferential portion and is adapted to form the gas hole. At least one of the first mold and the second mold has at least one first protrusion disposed radially outward of the center protrusion and in contact with a portion of the outer circumferential portion of the gas permeable member. At least one of the first mold and the second mold has at least one second protrusion disposed radially outward of the center protrusion and surrounding an outer peripheral edge of the gas permeable member. The method comprises a gas permeable member disposing step of disposing the gas permeable member radially inward of the second protrusion formed in at least one of the first mold and the second mold; a cavity forming step of forming the cavity by disposing the first mold and the second mold with the central portion of the gas permeable member sandwiched between the center protrusions of the first mold and the second mold; and a resin molding step of injecting the molten resin into the cavity for molding.

A casing of the present invention comprises the above-mentioned resin member with a gas permeable member.

A sensor of the present invention comprises the above-mentioned casing and a sensor element housed in the casing while facing the gas hole.

Effect of the Invention

According to the present invention, there can be obtained a resin member with a gas permeable member whose structure allows restraint of deformation of the gas permeable member, allows the gas permeable member to completely cover a gas hole, and allows easy checking to see whether or not the gas permeable member completely covers the gas hole.

MODES FOR CARRYING OUT THE INVENTION

Embodiments of the present invention will now be described.

Figure 1:
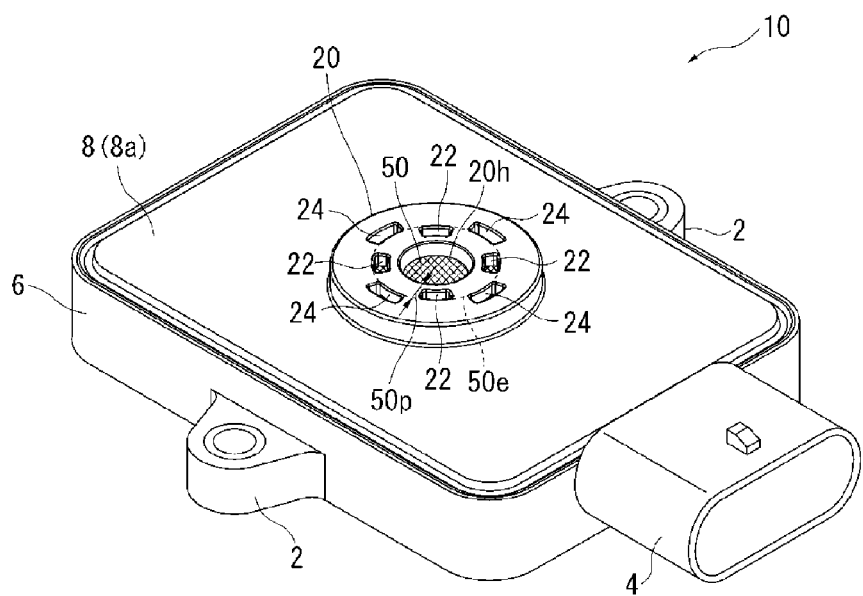
FIG. 1 is a perspective view of a case including a resin member with a gas permeable member according to a first embodiment of the present invention.
Figure 2:
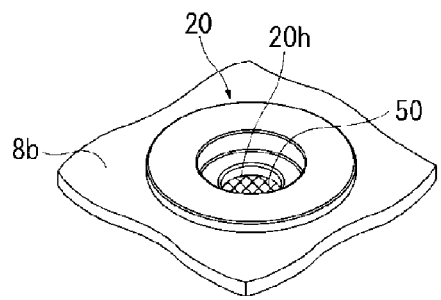
FIG. 2 is a fragmentary perspective view of a gas hole and its periphery of the resin member with a gas permeable member as viewed from the back side.
Figure 3:
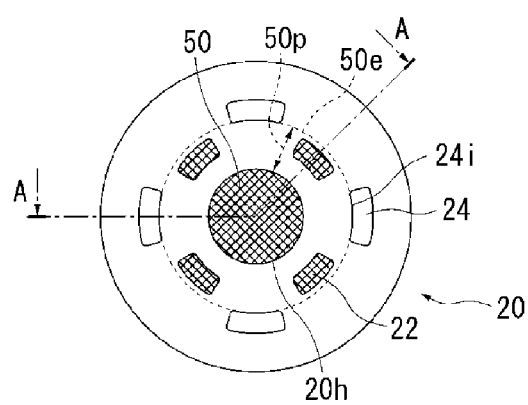
FIG. 3 is a top view of the gas hole and its periphery of the resin member with a gas permeable member as viewed from the front side.
Figure 4:
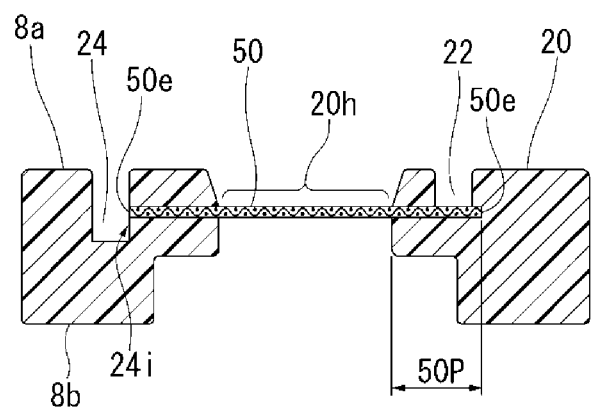
FIG. 4 is a sectional view taken along line A-A of FIG. 3.

FIG. 1 is a perspective view of a case 10 including a resin member with a gas permeable member 8 according to a first embodiment of the present invention; FIG. 2 is a fragmentary perspective view of a gas hole 20h and its periphery of the resin member with a gas permeable member 8 as viewed from the back side; FIG. 3 is a top view of the gas hole 20h and its periphery of the resin member with a gas permeable member 8 as viewed from a front surface 8a side; and FIG. 4 is a sectional view taken along line A-A of FIG. 3.

As shown in FIG. 1, a case 10 includes a casing main body portion 6 formed of resin by molding and having a generally rectangular box-like shape, and a generally flat top plate 8 which closes a top opening 6a (see FIG. 8) of the casing main body portion 6. The top plate 8 and the case 10 correspond to "a resin member with a gas permeable member" and "a casing," respectively, appearing in claims.

A flange portion 2 extends outward from a central portion of each of two long sides of the casing main body portion 6, and a bolt hole is formed at the center of each flange portion 2. Bolts (not shown) passing through the bolt holes are screwed into an object (for example, a predetermined portion of a vehicle), whereby the case 10 which houses a subject of housing (sensor element 60 (see FIG. 8)) is attached to the object. Also, a tubular connector portion 4 for exchanging signals with an external device extends outward from one short side of the casing main body portion 6.

Meanwhile, an annular member 20 projects upward from a central portion of a front surface 8a of the top plate 8. A single circular gas hole 20h is open in the annular member 20, and an ambient atmosphere flows between the inside and outside of the case 10 through the gas hole 20h. As will be described in detail later, the top plate 8 including the annular member 20 is formed around a circular sheet-like metal mesh 50 by means of insert molding; an outer circumferential portion 50p of the metal mesh 50 is embedded in resin used to form the annular member 20; and the metal mesh 50 covers the gas hole 20h in a gas permeable manner.

Notably, a water repellent filter (not shown) may be disposed on the lower side of the metal mesh 50 (inside the case 10) in such a manner as to cover the gas hole 20h for preventing entry of water into the case 10 through the gas hole 20h. Alternatively, the water repellent filter may be disposed on the upper side of the metal mesh 50 in such a manner as to cover the gas hole 20h.

Figure 8:
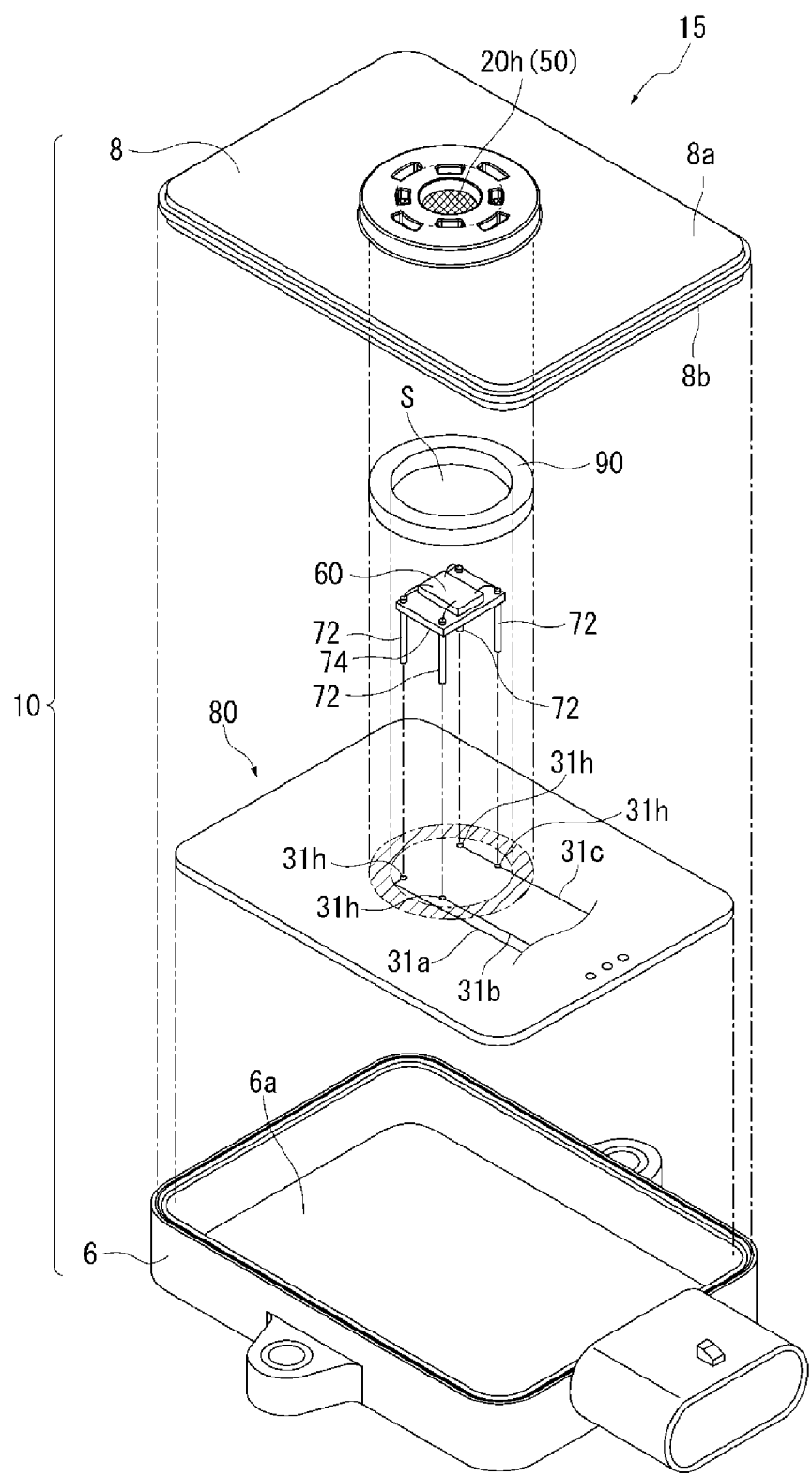
FIG. 8 is an exploded perspective view of a sensor according an embodiment of the present invention.

As shown in FIG. 8, which will be described later, the sensor element 60 disposed within the case 10 is a hydrogen gas sensor element. Also, the metal mesh 50 serves as a flame arrester which has an explosion prevention function. Therefore, even when the temperature of the sensor element 60 becomes higher than the ignition temperature of hydrogen gas and the hydrogen gas ignites inside the case 10, a produced flame is prevented from escaping to the outside of the case 10.

Notably, the "resin member with a gas permeable member" may at least partially constitute the case 10. In the case where the case 10 is composed of a plurality of members, the metal mesh 50 and a member having the gas hole 20h corresponds to the "resin member with a gas permeable member." Also, all members of the case 10 are not necessarily formed of resin. At least the "resin member with a gas permeable member;" specifically, the top plate 8, may be formed of resin. For example, the casing body portion 6 may be formed of metal. In the present embodiment, the top plate 8 is fixed to the casing body portion 6 with an adhesive, by fusing, or the like.

The gas permeable member (metal mesh 50) is larger in outline than the gas hole formed in the resin member as viewed in the front-back direction of the resin member.

The annular member 20 has four arced first recesses 22 depressed from the front surface 8a of the top plate 8 and disposed radially outward of the gas hole 20h and circumferentially at equal intervals at positions where the first recesses 22 partially coincide with the outer circumferential portion 50p of the metal mesh 50.

Also, the annular member 20 has four second recesses 24 depressed from the front surface 8a of the top plate 8 and disposed radially outward of the first recesses 22 in such a manner as to surround an outer peripheral edge 50e of the metal mesh 50.

Meanwhile, as shown in FIG. 2, the annular member 20 also protrudes from a central portion of a back surface 8b of the top plate 8, and the gas hole 20h opens in the annular member 20; however, the first recess and the second recess are not formed in the back surface 8b.

Next, with reference to FIGS. 3 and 4, the first recesses 22 and the second recesses 24 will be described.

First, as shown in FIG. 3, at least a portion of the metal mesh 50 (in the present embodiment, the metal mesh 50 is exposed at the entirety of the first recess 22) is exposed and visible through the first recesses 22 as viewed in the front-back direction (the thickness direction directed from the front surface 8a to the back surface 8b of the top plate 8). Specifically, as shown in FIG. 4, each of the first recesses 22 is depressed from the front surface 8a to such a depth as to reach the metal mesh 50, so that the metal mesh 50 is exposed and thus visible at the bottom of the first recess 22. Meanwhile, the first recesses 22 are disposed radially outward of the gas hole 20h at a position corresponding to the outer circumferential portion 50p (located radially inward of the outer peripheral edge 50e) of the metal mesh 50. Therefore, in the case where at least a portion of the metal mesh 50 is visible through the first recesses 22, this indicates that the outer peripheral edge 50e of the metal mesh 50 is located radially outward of the first recesses 22 and, in turn, the gas hole 20h; i.e., the metal mesh 50 completely covers the gas hole 20h.

Notably, as shown in FIGS. 5A-5D, which will be described later, in forming the top plate 8 by resin molding using a mold, the first recesses 22 are formed while top surfaces 122a of first protrusions 122 of the mold are in contact with the plane of the metal mesh 50. At this time, if resin molding is performed while a portion of the top surface(s) 122a is separated from the metal mesh 50 as a result of insufficient contact of the metal mesh 50 with the top surface(s) 122a, the metal mesh 50 is exposed at a portion of the bottom of the first recess(es) 22, whereas the metal mesh 50 is embedded in resin at the other portion of the bottom of the first recess(es) 22; thus, resin is visible at the other portion of the bottom of the first recess(es) 22. Even in this case, a portion of the metal mesh 50 is said to be visible through the first recess(es) 22.

By contrast, if the metal mesh 50 is not exposed and invisible through the first recess(es) 22 as viewed in the front-back direction, this indicates that the outer peripheral edge 50e of the metal mesh 50 is located between the first recess(es) 22 and the gas hole 20h; i.e., the metal mesh 50 may possibly fail to be embedded in resin to form a gap between the metal mesh 50 and the inner circumference of the gas hole 20h.

Thus, by means of observing the first recesses 22 in the front-back direction, whether or not the metal mesh 50 completely covers the gas hole 20h can be easily checked. The metal mesh 50 may be visually observed through the first recesses 22; however, the metal mesh 50 can be automatically observed by predetermined image recognition or the like. Although described in detail later, in the course of injection molding, the first recesses 22 support the plane of the metal mesh 50 and have a function of restraining the metal mesh 50 from bending within a mold as a result of subjection to molding pressure of molten resin.

Next, as shown in FIG. 3, the metal mesh 50 is invisible through the second recesses 24 as viewed in the front-back direction. Specifically, as shown in FIG. 4, since each of the second recesses 24 is depressed from the front surface 8a in such a manner that an inner side surface 24i thereof surrounds the outer peripheral edge 50e of the metal mesh 50 from radially outside, the metal mesh 50 is not exposed at the bottom of the second recess 24 and is thus invisible.

Meanwhile, as will be described later, the second recesses 24 are portions which are not filled with resin because of existence of cores (protrusions) in a mold in the course of molding the top plate 8, and the protrusions surround the outer peripheral edge 50e of the metal mesh 50 to thereby prevent a positional shift of the metal mesh 50 in a planar direction in the course of injection molding. Therefore, the second recesses 24 have a function of preventing a positional shift of the metal mesh 50 in a planar direction in the course of molding. As mentioned above, since the second recesses 24 are formed by the cores which surround the metal mesh 50 from radially outside, as shown in FIG. 4, the second recesses 24 are depressed from the front surface 8a to a depth deeper than that of the metal mesh 50 and are depressed deeper than the first recesses 22. However, as will be described later, the depth relation "first recess<second recess" may not hold as in the case where the first recesses are formed in the front surface, whereas the second recesses are formed in the back surface.

In the present embodiment, on a plane onto which the gas permeable member (metal mesh 50) and the second recesses 24 are projected in the front-back direction, the second recesses 24 are disposed at positions on an imaginary outline formed by radially expanding the outline of the gas permeable member (metal mesh 50).

Notably, a state in which the second recesses 24 "surround" the outer peripheral edge 50e of the metal mesh 50 means a state in which the inner side surfaces 24i of the second recesses 24 are in contact with the outer peripheral edge 50e of the metal mesh 50 or a state in which the second recesses 24 are disposed radially outward of the outer peripheral edge 50e such that resin fills a region therebetween. In the case where the second recesses 24 are in contact with the outer peripheral edge 50e of the metal mesh 50, as shown in FIG. 4, the outer peripheral edge 50e of the metal mesh 50 is visible at the inner side surfaces 24i of the second recesses 24; however, the metal mesh 50 is invisible through the second recesses 24 as viewed from the "front-back" direction.

In this manner, the invisible state indicates that although the outer peripheral edge 50e of the metal mesh 50 is visible at the inner side surfaces 24i of the second recesses 24, the outer peripheral edge 50e does not protrude from the inner side surfaces 24i of the second recesses 24, and thus the metal mesh 50 is invisible as viewed in the front-back direction, or that the metal mesh 50 is not exposed at the inner side surfaces 24i of the second recesses 24.

Figure 6:
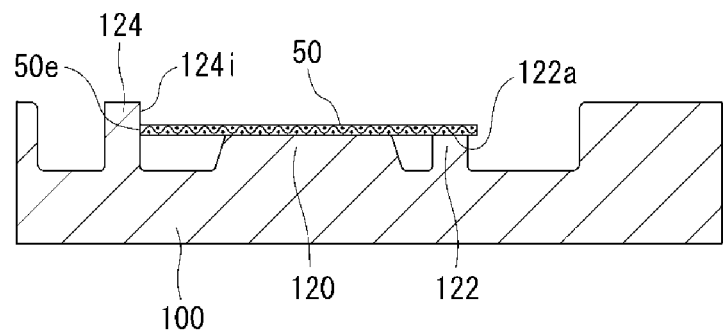
FIG. 6 is a sectional view taken along line B-B of FIG. 5B.
Figure 7:
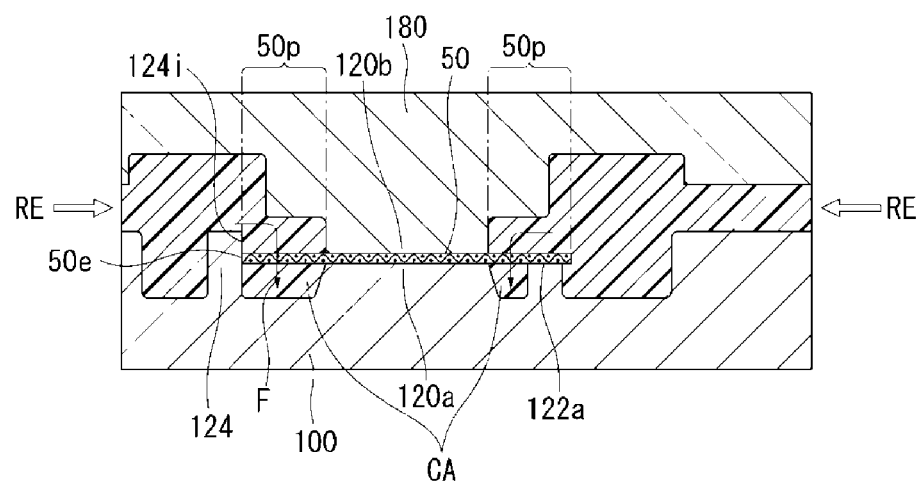
FIG. 7 is a sectional view taken along line C-C of FIG. 5C.

Next, with reference to FIGS. 5A-5D to 7, a method of manufacturing the top plate 8 will be described. FIGS. 5A-5D are process drawings showing steps of manufacturing the top plate 8; FIG. 6 is a sectional view taken along line B-B of FIG. 5B; and FIG. 7 is a sectional view taken along line C-C of FIG. 5C. FIGS. 5A-5D to 7 show only the annular member 20 and its periphery; however, needless to say, the top plate 8 including the annular member 20 is resin-molded at a time.

Figure 5:
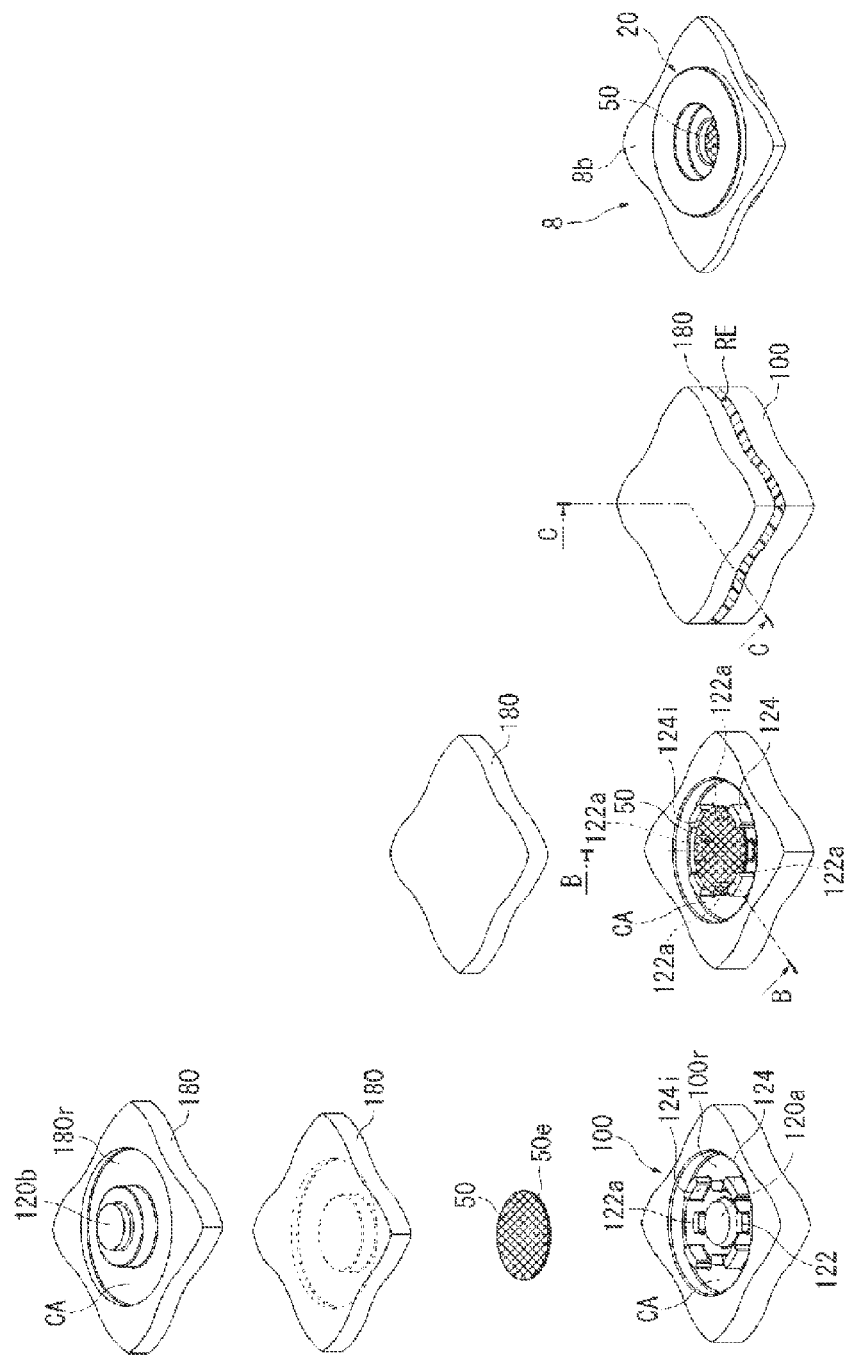
FIGS. 5A-5D are process drawings showing steps of manufacturing a top plate 8.

First, as shown in FIG. 5A, a lower mold 100, an upper mold 180, and the metal mesh 50 are prepared. The lower mold 100 and the upper mold 180 correspond to "a first mold" and "a second mold," respectively, appearing in claims.

The lower mold 100 has a circular columnar recess 100r; a circular columnar center protrusion 120a protruding upward from the center of the recess 100r; the four arc columnar first protrusions 122 protruding upward from the recess 100r at positions located radially outward of the center protrusion 120a and at circumferentially equal intervals; and four arc columnar second protrusions 124 protruding upward from the recess 100r at positions located radially outward of the first protrusions 122 and at circumferentially equal intervals.

The second protrusions 124 protrude higher than do the first protrusions 122. Inner side surfaces 124i of the second protrusions 124 are located on the circumference of a circle slightly greater in diameter than that of the outer peripheral edge 50e of the metal mesh 50, thereby allowing the metal mesh 50 to be set radially inward of the second protrusions 124.

Meanwhile, the upper mold 180 has a circular columnar recess 180r and a stepped circular columnar center protrusion 120b protruding upward from the center of the recess 180r. The upper mold 180 is disposed above the lower mold 100 with a predetermined gap formed therebetween. Molten resin is injected, for molding, into a cavity CA formed between the lower mold 100 and the upper mold 180, whereby the top plate 8 can be resin-molded.

The recess 100r partially constitutes the cavity CA and forms the annular member 20 on the front surface 8a side in FIG. 1. The center protrusion 120a, the first protrusions 122, and the second protrusions 124 form the gas hole 20h, the first recesses 22, and the second recesses 24, respectively, on the front surface 8a side. A region (excluding the first protrusions 122) located radially inward of the second protrusions 124 partially constitutes the cavity CA, and the outer circumferential portion 50p (see FIG. 1) of the metal mesh 50 is embedded in resin in the region.

Also, the recess 180r partially constitutes the cavity CA and forms the annular member 20 on the back surface 8b side in FIG. 1. The center protrusion 120b forms the gas hole 20h on the back surface 8b side.

Next, as shown in FIG. 5B and FIG. 6, the metal mesh 50 is disposed radially inward of the second protrusions 124 of the lower mold 100 (gas permeable member disposing step). The first protrusions 122 stand upright at positions located radially inward of the second protrusions 124, and the top surfaces 122a of the first protrusions 122 come into contact with the lower plane (plane which faces the front surface 8a side after molding) of the metal mesh 50.

Next, as shown in FIG. 5C and FIG. 7, the upper mold 180 is disposed above the lower mold 100 with a predetermined gap formed therebetween such that a central portion of the metal mesh 50 is sandwiched between the center protrusions 120a and 120b of the lower mold 100 and the upper mold 180, respectively, thereby forming the cavity CA between the lower mold 100 and the upper mold 180. Then, molten resin RE is injected into the cavity CA for molding, whereby the top plate 8 shown in FIG. 5D can be manufactured.

As shown in FIG. 7, in the course of injecting the molten resin RE for molding, since the outer peripheral edge 50e of the metal mesh 50 abuts against the inner side surfaces 124i of the second protrusions 124 from inside, a planar movement of the metal mesh 50 is restricted, whereby there can be prevented a positional shift of the metal mesh 50 from the position of the center protrusions 120a and 120b, which is to become the position of the gas hole.

At a portion of the cavity CA around the outer circumferential portion 50p of the metal mesh 50, since the molten resin RE flows at a predetermined molding pressure F in the thickness direction of the metal mesh 50 (downward in FIG. 7), the molding pressure F may possibly cause the metal mesh 50 to be deformed. In this connection, the top surfaces 122a of the first protrusions 122 are in contact with the lower plane of the metal mesh 50 to thereby cope with the molding pressure F, whereby the deformation of the metal mesh 50 can be restrained.

As mentioned above, since the occurrence of product defects is reduced by restraining the deformation and positional shift of the metal mesh 50 in the course of molding, yield can be improved. Also, since the positional shift of the metal mesh 50 in the course of molding is prevented, the metal mesh 50 can completely covers the gas hole 20h; thus, the gas permeable member can reliably exhibits a predetermined effect (explosion prevention function or the like).

The first recesses 22 and the second recesses 24 cause reduction in associated wall thickness due to depression and thus cause reduction in strength. Thus, in the case where the first recesses 22 and the second recesses 24 overlap one another with respect to a circumferential position, overlapping regions may possibly greatly reduce in strength. However, in the present embodiment, since the first recesses 22 and the second recesses 24 are arranged not to overlap one another with respect to a circumferential position, reduction in strength can be prevented.

In the present embodiment, the first recesses 22 and the second recesses 24 are formed in only one (front surface 8a) of two opposed surfaces of the top plate 8, and the first recesses 22 and the second recesses 24 do not extend between the front surface 8a and the back surface 8b. Thus, as shown in FIG. 2, an outer peripheral portion (annular member 20) around the gas hole 20h on the back surface 8b side becomes flat, and through utilization of the flat surface, various components can be disposed. For example, as shown in FIG. 8, an annular elastic seal member 90 can be bonded to the surface (annular member 20).

Next, with reference to FIG. 8, a sensor 15 having the sensor element 60 housed in the case 10 will be described.

The sensor 15 includes the sensor element 60, a circuit board 80, and the above-described case 10 for housing the sensor element 60 and the circuit board 80. The sensor element 60 is disposed (mounted) on the upper surface of the circuit board 80 via a pedestal 74. A plurality of (four in this example) electrodes of the sensor element 60 are connected, through bonding wires, to corresponding connection terminals 72 protruding downward from the four corners of the pedestal 74. When the circuit board 80 is positioned and disposed in the casing main body portion 6, and the top plate 8 is fitted to the inner edge of the top opening 6a of the casing main body portion 6, the annular elastic seal member 90 bonded to the annular member 20 on the back surface 8b side of the top plate 8 presses the upper surface of the circuit board 80 to thereby fix the circuit board 80.

A microcomputer and various types of electronic components (not shown) for controlling the sensor element 60 are mounted on the circuit board 80 by means of soldering or the like. Also, a plurality of wiring traces 31a to 31c for electrical connection with the sensor element 60 are formed on the circuit board 80, and four through-holes 31h are formed at the one-end side of the wiring traces 31a to 31c. The connection terminals 72 are inserted through the corresponding through-holes 31h to thereby electrically connect the sensor element 60 to the circuit board 80, and the wiring traces 31a to 31c are led to an external device through the connector portion 4.

The inner space of the case 10 surrounded by the surface of the circuit board 80, the wall surface of the gas hole 20h, and the inner surface of the elastic seal member 90 form a measurement chamber S in which the sensor element 60 is present and which communicates with the atmosphere to be detected. The concentration of hydrogen gas contained in the atmosphere to be detected within the measurement chamber S is detected by the sensor element 60.

Figure 9:
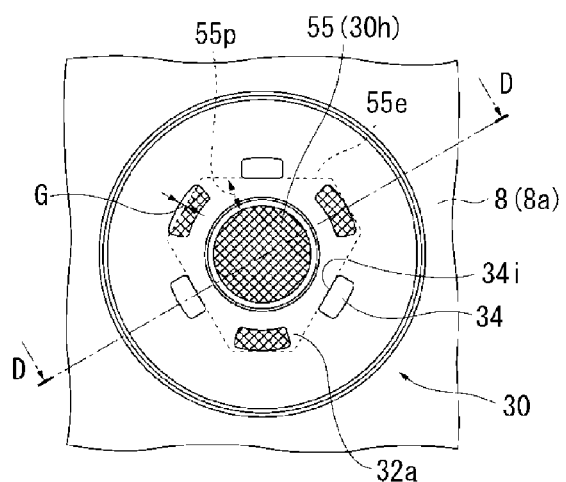
FIG. 9 is a top view of a gas hole and its periphery of a resin member with a gas permeable member according to a second embodiment of the present invention as viewed from the front side.
Figure 10:
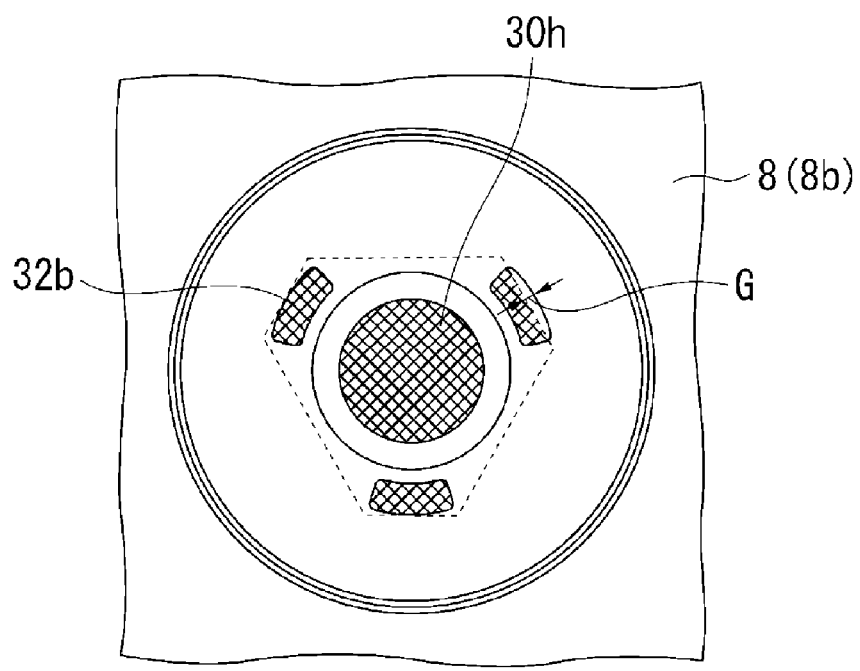
FIG. 10 is a top view of the gas hole and its periphery as viewed from the back side.

Next, with reference to FIGS. 9 to 11, a resin member with a gas permeable member according to a second embodiment of the present invention will be described. FIG. 9 is a top view of a gas hole 30h and its periphery of the resin member with a gas permeable member according to the second embodiment of the present invention as viewed from the front surface 8a side; FIG. 10 is a top view of the gas hole 30h and its periphery as viewed from the back surface 8b side; and FIG. 11 is a sectional view taken along line D-D of FIG. 9.

The configurational features of the resin member with a gas permeable member according to the second embodiment are similar to those of the first embodiment except a metal mesh 55 and an annular member 30 including first recesses 32a and 32b and second recesses 34; thus, like configurational features are unillustrated or denoted by like reference numerals, and repeated description thereof is omitted. Also, only the annular member 30 and its periphery of the top plate 8 is illustrated.

Figure 11:
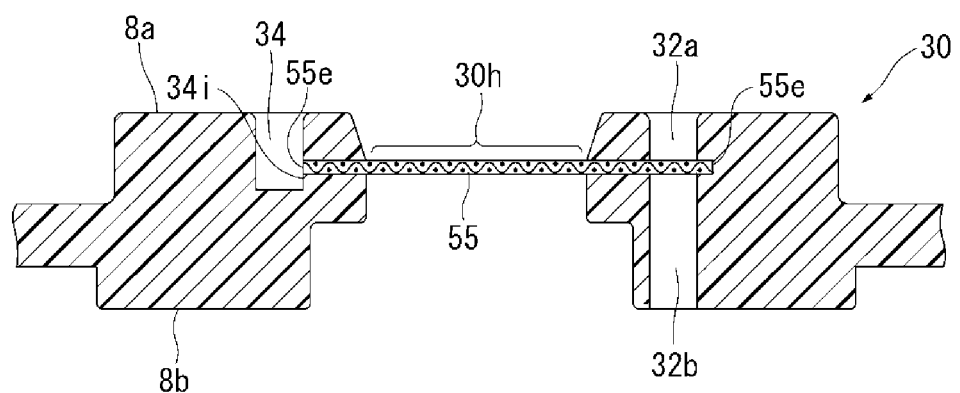
FIG. 11 is a sectional view taken along line D-D of FIG. 9.

As shown in FIGS. 9 and 11, the metal mesh 55 has the form of a sheet having such a hexagonal shape that an equilateral triangle is truncated at apexes to form short sides.

Also, as shown in FIG. 9, the top plate 8 has the annular member 30, similar to that in the first embodiment, formed at its central portion, and a circular gas hole 30h opens in the annular member 30. An outer perimetric portion 55p of the metal mesh 55 is embedded in resin used to form the annular member 30, and the metal mesh 55 covers the gas hole 30h in a gas permeable manner.

The annular member 30 has three arced first recesses 32a depressed from the front surface 8a of the top plate 8 and disposed radially outward of the gas hole 30h and circumferentially at equal intervals in a region corresponding to the outer perimetric portion 55p of the metal mesh 55. Also, the annular member 30 has three arced second recesses 34 depressed from the front surface 8a of the top plate 8 and disposed circumferentially at equal intervals in such a manner as to circumferentially alternate with the first recess 32a on the same circumference of a circle.

The first recesses 32a are disposed in parallel with the corresponding above-mentioned short sides of the metal mesh 55. The second recesses 34 are disposed in parallel with the corresponding long sides of the metal mesh 55 and surround an outer peripheral edge 55e of the metal mesh 55 from outside at positions corresponding to central portions of the long sides.

Meanwhile, as shown in FIG. 10, the annular member 30 protrudes from a central portion of the back surface 8b of the top plate 8, and the gas hole 30h opens in the annular member 30. Furthermore, three first recesses 32b are disposed in the back surface 8b in such a manner as to be aligned with the corresponding first recesses 32a; however, the second recesses are not formed.

In this manner, in the second embodiment, the first recesses 32a and 32b cooperatively extend between the front surface 8a and the back surface 8b with the metal mesh 55 existing therebetween (see FIG. 11). However, since the first recesses 32a and 32b are depressed from the front surface 8a and the back surface 8b, respectively, to such a depth as to reach the metal mesh 55, the second recesses 34 are depressed deeper than the first recesses 32a.

At least a portion of the metal mesh 55 is exposed and visible through the first recesses 32a and 32b as viewed in the front-back direction. Since the first recesses 32a and 32b are disposed radially inward of the outer peripheral edge 55e of the metal mesh 55, also in the second embodiment, by means of observing the first recesses 32a and 32b in the front-back direction, whether or not the metal mesh 55 completely covers the gas hole 30h can be easily checked.

Also, since the second recesses 34 are depressed in such a manner that inner side surfaces 34i thereof surround the outer peripheral edge 55e of the metal mesh 55 from radially outside, the metal mesh 50 is not exposed at the bottoms of the second recesses 34 and is thus invisible, and, in the course of molding, the metal mesh 55 is prevented from positionally shifting in a planar direction.

As shown in FIGS. 9 and 10, in the second embodiment, the metal mesh 55 is visible at a portion of one first recess 32a and at a portion of the first recess 32b aligned with the one first recess 32a such that a gap G is formed between the metal mesh 55 and the outer edges of the first recesses 32a and 32b and is not covered with the metal mesh 55. The gap G may possibly be formed, for example, when the metal mesh 55 becomes short due to dimensional variations or is somewhat bent in the course of injection molding.

In the second embodiment, since the first recesses 32a and 32b extend between the front surface 8a and the back surface 8b with the metal mesh 55 existing therebetween, gas can flow through the gap G instead of passing through the metal mesh 50. Even in this case, no problem arises by means of establishing space isolation between the measurement chamber S and the gap G; for example, by means of bonding the annular elastic seal member 90 shown in FIG. 8 onto the first recesses 32b to thereby close the gap G or by means of attaching the elastic seal member 90 to a region located radially inward of the first recesses 32a and 32b. Alternatively, a water repellent filter may be disposed in such a manner to cover the first recesses 32a and 32b, which extend between the front surface 8a and the back surface 8b, for preventing entry of water into the interior of the case 10 through the first recesses 32a and 32b.

Meanwhile, in the second embodiment, since the first recesses 32a and 32b can be observed from both of the front surface 8a and the back surface 8b, whether or not the metal mesh 55 completely covers the gas hole 30h can be more easily checked. Therefore, whether or not the first recesses 32a and 32b are rendered to extend between the front surface 8a and the back surface 8b may be determined according to intended use, the shape of the case 10, etc.

Similarly, when the second recesses 34 (24) are rendered to extend between the front surface 8a and the back surface 8b, the second recesses 34 (24) become through-holes; however, even in this case, no problem arises by means of establishing space isolation between the second recesses 34 and the gas hole 30h, which is located radially inward of the second recesses 34. Also, a water repellent filter may be disposed in such a manner as to cover the second recesses 34 (24) extending between the front surface 8a and the back surface 8b, for preventing entry of water into the interior of the case 10 through the second recesses 34 (24). Therefore, whether or not the second recesses 34 are rendered to extend between the front surface 8a and the back surface 8b may be determined according to intended use, the shape of the case 10, etc. However, preferably, the second recesses 34 (24) assume the form of grooves which do not extend between the front surface 8a and the back surface 8b.

Next, with reference to FIGS. 12A-12D and 13, a method of manufacturing a resin member with a gas permeable member (top plate 8) according to a second embodiment of the present invention will be described. FIGS. 12A-12D are process drawings showing steps of manufacturing the top plate 8 according to the second embodiment, and FIG. 13 is a sectional view taken along line E-E of FIG. 12C. FIGS. 12A-12D to 13 show only the annular member 30 and its periphery; however, needless to say, the top plate 8 including the annular member 30 is resin-molded at a time.

Figure 12:
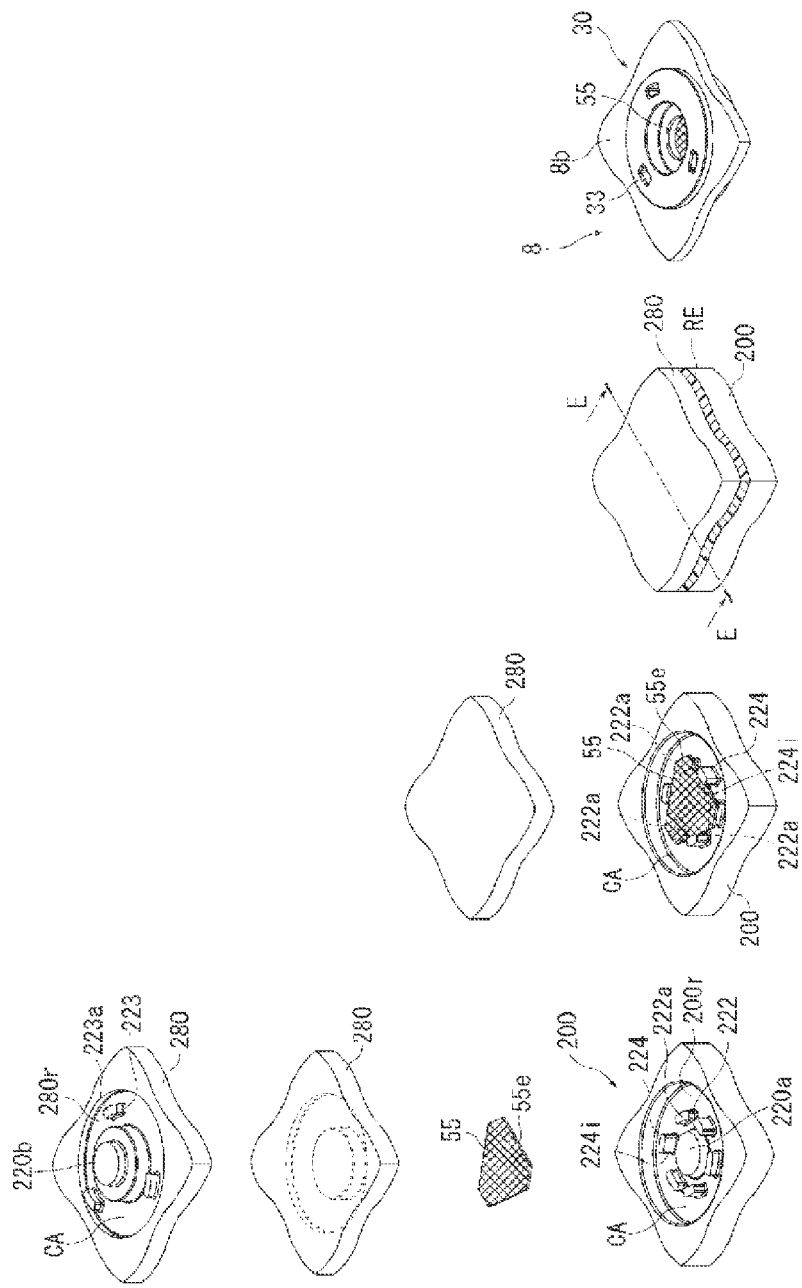
FIGS. 12A-12D are process drawings showing steps of manufacturing a top plate 8 according to the second embodiment.
Figure 13:
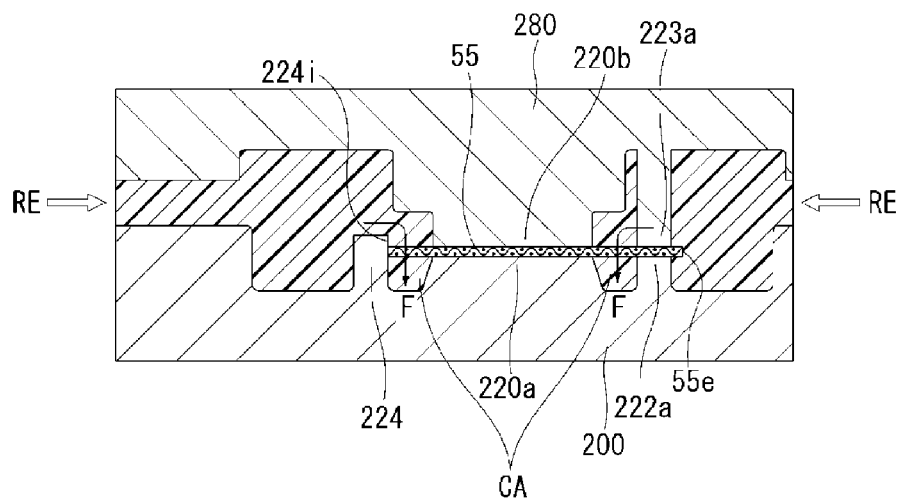
FIG. 13 is a sectional view taken along line E-E of FIG. 12C.

First, as shown in FIG. 12A, a lower mold 200, an upper mold 280, and the metal mesh 55 are prepared. The lower mold 200 and the upper mold 280 correspond to "a first mold" and "a second mold," respectively, appearing in claims.

The lower mold 200 has a circular columnar recess 200r; a circular columnar center protrusion 220a protruding upward from the center of the recess 200r; three arc columnar first protrusions 222 protruding upward from the recess 200r at positions located radially outward of the center protrusion 220a and at circumferentially equal intervals; and three arc columnar second protrusions 224 protruding upward from the recess 200r at circumferentially equal intervals.

The second protrusions 224 are disposed in such a manner as to circumferentially alternate with the first protrusions 222 on the same circumference of a circle. The second protrusions 224 protrude higher than do the first protrusions 222.

Meanwhile, the upper mold 280 has a circular columnar recess 280r, a stepped circular columnar center protrusion 220b protruding upward from the center of the recess 280r, and three arc columnar first protrusions 223 protruding upward from the recess 280r at positions located radially outward of the center protrusion 220b and at circumferentially equal intervals. The upper mold 280 is disposed above the lower mold 200 with a predetermined gap formed therebetween. Molten resin is injected, for molding, into the cavity CA formed between the lower mold 200 and the upper mold 280, whereby the top plate 8 according to the second embodiment can be resin-molded.

The recess 200r partially constitutes the cavity CA and forms the annular member 30 on the front surface 8a side in FIG. 9. The center protrusion 220a, the first protrusions 222, and the second protrusions 224 form the gas hole 30h, the first recesses 32a, and the second recesses 34, respectively, on the front surface 8a side. A region (excluding the first protrusions 222) located radially inward of the second protrusions 224 partially constitutes the cavity CA, and the outer circumferential portion 55p (see FIG. 9) of the metal mesh 55 is embedded in resin in the region.

Also, the recess 280r partially constitutes the cavity CA and forms the annular member 30 on the back surface 8b side in FIG. 9. The center protrusion 220b and the first protrusions 223 form the gas hole 30h and the first recesses 32b, respectively, on the back surface 8b side.

Next, as shown in FIG. 12B, the metal mesh 55 is disposed radially inward of the second protrusions 224 of the lower mold 200 (gas permeable member disposing step). At this time, top surfaces 222a of the first protrusions 222 come into contact with the lower plane (plane which faces the front surface 8a side after molding) of the metal mesh 55 (see FIG. 13).

Next, the upper mold 280 is disposed above the lower mold 200 with a predetermined gap formed therebetween such that a central portion of the metal mesh 55 is sandwiched between the center protrusions 220a and 220b of the lower mold 200 and the upper mold 280, respectively, thereby forming the cavity CA between the lower mold 200 and the upper mold 280. Then, molten resin RE is injected into the cavity for molding as shown in FIG. 12C, whereby the top plate 8 according to the second embodiment shown in FIG. 12D can be manufactured.

As shown in FIG. 13, in the course of injecting the molten resin RE for molding, since the outer peripheral edge 55e of the metal mesh 55 abuts against the inner side surfaces 224i of the second protrusions 224 from inside, a planar movement of the metal mesh 55 is restricted, whereby there can be prevented a positional shift of the metal mesh 55 from the position of the center protrusions 220a and 220b, which is to become the position of the gas hole.

At a portion of the cavity CA around the outer circumferential portion 55p of the metal mesh 55, since the molten resin RE flows at a predetermined molding pressure F in the thickness direction of the metal mesh 55 (downward in FIG. 13), the molding pressure F may possibly cause the metal mesh 55 to bend. In this connection, the top surfaces 222a of the first protrusions 222 are in contact with the lower plane of the metal mesh 55 to thereby cope with the molding pressure F, whereby the deformation of the metal mesh 55 can be restrained.

Furthermore, in the second embodiment, the upper mold 280 also has the first protrusions 223, and, while firmly holding the metal mesh 55 therebetween, the lower and upper first protrusions 222 and 223 cope with the molding pressure F; therefore, the deformation of the metal mesh 55 can be further restrained. Depending on the shape of the cavity CA or the like, the molten resin RE may flow opposite the direction of FIG. 13 (upward); however, according to the second embodiment, the upper and lower planes of the metal mesh 55 are held between the top surfaces 222a and 223a of the first protrusions 222 and 223 of the metal mesh 55 to thereby cope with the molding pressure F. Thus, the deformation of the metal mesh 55 can be restrained regardless of the direction of flow of the molten resin RE.

The present invention is not limited to the above embodiments, but extends into various modifications and equivalents encompassed by the ideas and scope of the invention.

Figure 14:
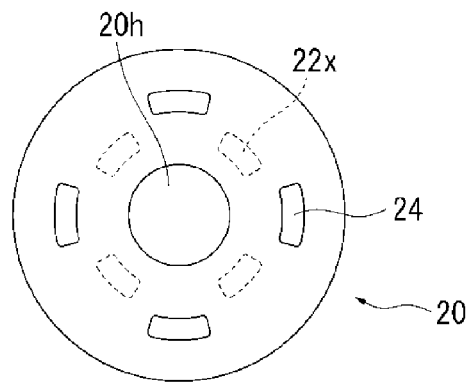
FIG. 14 is a top view showing another embodiment of a resin member with a gas permeable member.

For example, in the above-described first embodiment, the first recesses 22 and the second recesses 24 are formed in the same surface (front surface 8a); however, as shown in FIG. 14, for example, the second recesses 24 may be formed in the front surface 8a, and first recesses 22x may be formed in the opposite surface (back surface 8b).

Figure 15:
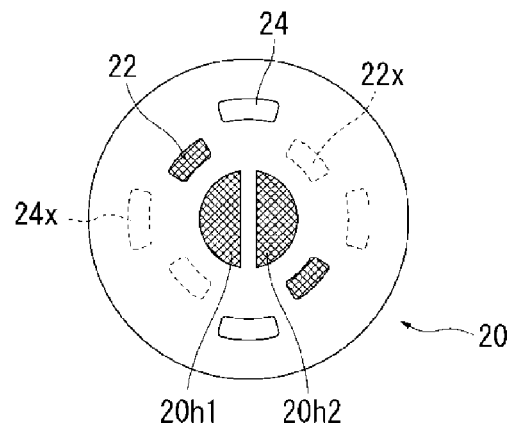
FIG. 15 is a top view showing a further embodiment of a resin member with a gas permeable member.

Also, as shown in FIG. 15, for example, the first recesses 22 and the first recesses 22x may be alternatingly formed on the front surface 8a side and on the back surface 8b side along the circumferential direction. Similarly, the second recesses 24 and second recesses 24x may be alternatingly formed on the front surface 8a side and on the back surface side 8b along the circumferential direction. Furthermore, no particular limitation is imposed on the number of gas holes; for example, instead of one gas hole, two gas holes 20h1 and 20h2 may be formed.

Figure 16:
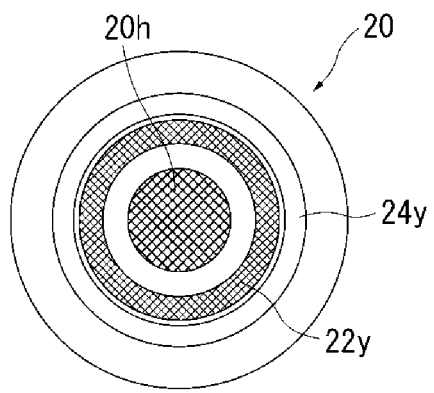
FIG. 16 is a top view showing a still further embodiment of a resin member with a gas permeable member.

Also, as shown in FIG. 16, for example, either one or both of first recess 22y and second recess 24y may assume the form of a circumferentially continuous annular groove. However, in the case where the first recess extends between the front surface and the back surface, imparting an annular form to the first recess results in deterioration in strength, since resin does not exist in the first recess; therefore, instead of assuming an annular form, the first recesses need to be formed at circumferential intervals.

Figure 17:
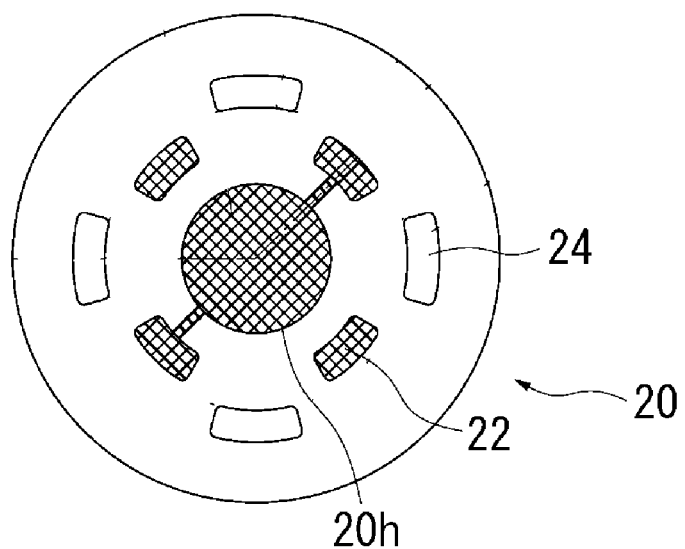
FIG. 17 is a top view showing yet another embodiment of a resin member with a gas permeable member.

In the above-described embodiment, the first recesses 22 and the gas hole 20h are separated from each other. However, the present invention is not limited thereto; for example, as shown in FIG. 17, the first recesses 22 and the gas hole 20h may be partially connected to each other.

The gas permeable member and the number and shape of the first and second recesses are not limited to those in the above-described embodiments. Also, the gas permeable member is not limited to the metal mesh, but may be, for example, a gas permeable resin filter or the like.

In the above-described embodiments, the sensor 15 is a hydrogen gas sensor which is one type of gas sensor. However, the sensor 15 may be a flammable gas sensor in which, for example, an oxide semiconductor, a heat generation resistor, or a heat conduction element is used. Also, the sensor 15 is not limited to a gas sensor, and may be other types of sensors such as a temperature sensor and a humidity sensor.

DESCRIPTION OF REFERENCE NUMERALS

8: resin member with gas permeable member
8a: front surface of resin member with gas permeable member
8b: back surface of resin member with gas permeable member
10: case
15: sensor
20h, 30h: gas hole
22, 32a, 32b: first recess
24, 34: second recess
50, 55: gas permeable member
50p, 55p: outer circumferential portion of gas permeable member
50e, 55e: outer peripheral edge of gas permeable member
60: sensor element
100, 200: first mold
120a, 120b, 220a, 220b: center protrusion
122, 222, 223: first protrusion
124, 224: second protrusion
180, 280: second mold
CA: cavity
RE: molten resin

The invention claimed is:

1. A resin member with a gas permeable member comprising:
   a resin member having at least one gas hole extending therethrough between a front surface and a back surface thereof, and
   a sheet-like gas permeable member being larger in outline than the at least one gas hole and covering the at least one gas hole in a gas permeable manner,
   an outer circumferential portion of the gas permeable member being embedded in the resin member,
   the resin member further comprising the following (i) and ii:
   (i) at least one of:
      a first recess disposed around the at least one gas hole, depressed from the front surface or the back surface of the resin member, and allowing at least a portion of a front surface or a back surface of the gas permeable member to be visible therethrough in a front-back direction, and
      a first through hole, disposed around the at least one gas hole, extending from the front surface to the back surface of the resin member and allowing the at least the portion of the front surface and the back surface of the gas permeable member to be visible therethrough in the front-back direction, and
   (ii) at least one of:
      a second recess which is disposed externally of an outer peripheral edge of the gas permeable member and depressed from the front surface or the back surface of the resin member and through which the front surface or the back surface of the gas permeable member is invisible in the front-back direction, and
      a second through hole, extending from the front surface to the back surface of the resin member, which is disposed externally of the outer peripheral edge of the gas permeable member and through which the front surface and the back surface of the gas permeable member are invisible in the front-back direction.

2. The resin member with the gas permeable member according to claim 1, wherein (i) the at least one of the first recess and the first through hole and (ii) the at least one of the second recess and the second through hole do not overlap each other as viewed from the center of the at least one gas hole in a direction orthogonal to a direction directed from the front surface to the back surface of the resin member.

3. A casing comprising the resin member with the gas permeable member according to claim 1 and a casing main body portion having an opening, wherein the resin member with the gas permeable member is disposed on the casing main body portion so as to close the opening.

4. A sensor comprising the casing according to claim 3 and a sensor element housed in the casing while facing the at least one gas hole.

5. A method of manufacturing a resin member with a gas permeable member by injecting molten resin, for molding, into a cavity formed between a first mold and a second mold, the resin member comprising a resin member having at least one gas hole extending therethrough between a front surface and a back surface thereof, and a sheet-like gas permeable member being larger in outline than the at least one gas hole and covering the at least one gas hole in a gas permeable manner, an outer circumferential portion of the gas permeable member being embedded in the resin member, the resin member further comprising the following (i) and (ii):

(i) at least one of:
a first recess disposed around the at least one gas hole, depressed from the front surface or the back surface of the resin member, and allowing at least a portion of a front surface or a back surface of the gas permeable member to be visible therethrough in a front-back direction, and
a first through hole, disposed around the at least one gas hole, extending from the front surface to the back surface of the resin member and allowing the at least the portion of the front surface and the back surface of the gas permeable member to be visible therethrough in the front-back direction, and (ii) at least one of:
a second recess which is disposed externally of an outer peripheral edge of the gas permeable member and depressed from the front surface or the back surface of the resin member and through which the front surface or the back surface of the gas permeable member is invisible in the front-back direction, and
a second through hole, extending from the front surface to the back surface of the resin member, which is disposed externally of the outer peripheral edge of the gas permeable member and through which the front surface and the back surface of the gas permeable member are invisible in the front-back direction the first mold and the second mold having respectively at least one center protrusion which comes into contact with a central portion of the gas permeable member excluding the outer circumferential portion and is adapted to form the gas hole, at least one of the first mold and the second mold having at least one first protrusion disposed radially outward of the center protrusion and in contact with a portion of the outer circumferential portion of the gas permeable member, and at least one of the first mold and the second mold having at least one second protrusion disposed radially outward of the center protrusion and surrounding an outer peripheral edge of the gas permeable member, the method comprising:
a gas permeable member disposing step of disposing the gas permeable member radially inward of the second protrusion formed in at least one of the first mold and the second mold;
a cavity forming step of forming the cavity by disposing the first mold and the second mold with the central portion of the gas permeable member sandwiched between the center protrusions of the first mold and the second mold; and
a resin molding step of injecting the molten resin into the cavity for molding.

* * * * *